United States Patent [19]

Steiner

[11] Patent Number: 4,562,004
[45] Date of Patent: Dec. 31, 1985

[54] 2,3,5,6-TETRASUBSTITUTED P-BENZOQUINONES AND THEIR PREPARATION

[75] Inventor: Gerd Steiner, Kirchheim, Fed. Rep. of Germany

[73] Assignee: BASF Aktiengesellschaft, Fed. Rep. of Germany

[21] Appl. No.: 588,973

[22] Filed: Mar. 14, 1984

[51] Int. Cl.$^4$ .................. C07C 50/06; C07C 153/11
[52] U.S. Cl. .............. 260/396 R; 260/455 R
[58] Field of Search .................. 260/396 R

[56] References Cited

U.S. PATENT DOCUMENTS 2,608,561  8/1952  Ragnar et al. ............ 260/396 R
4,229,478 10/1980  Jones et al. ............. 260/396 R
4,362,727 12/1982  Steiner et al. ........... 424/248.51

OTHER PUBLICATIONS

Chemical Abstracts 82 97960 s, (1975).
Morrison and Boyd, *Organic Chemistry*, 3 ed, 1974, pp. 372-373.

D. W. H. Mac Dowell and J. C. Wisowaty, J. Org. Chem. 37 (1972), 1712.

*Primary Examiner*—Glennon H. Hollrah
*Assistant Examiner*—Raymond Covington
*Attorney, Agent, or Firm*—Keil & Weinkauf

[57] ABSTRACT

2,3,5,6-Tetrasubstituted p-benzoquinones of the formula I

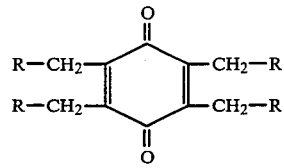

where R is bromine, $C_2$–$C_6$-acylthio or benzoylthio, their preparation and their use for the preparation of 4,8-dihydrobenzo[1,2-c:4,5-c']dithiophene-4,8-dione are described.

11 Claims, No Drawings

2,3,5,6-TETRASUBSTITUTED P-BENZOQUINONES AND THEIR PREPARATION

The invention relates to novel 2,3,5,6-tetrasubstituted p-benzoquinones, their preparation and their use for the preparation of 4,8-dihydrobenzo[1,2-c:4,5-c']- dithiophene-4,8-dione.

The preparation of 4,8-dihydrobenzo[1,2-c:4,5-c']dithiophene-4,8-dione by the method used hitherto, and due to D. W. H. Mac Dowell and J. C. Wisowaty, J. Org. Chem. 37 (1972), 1712, is tedious and, particularly for relatively large batches, gives very moderate yields.

We have found that 4,8-dihydrobenzo[1,2-c:4,5-c']dithiophene-4,8-dione can be obtained from novel compounds in a relatively simple manner.

The present invention relates to 2,3,5,6-tetrasubstituted p-benzoquinones of the formula I

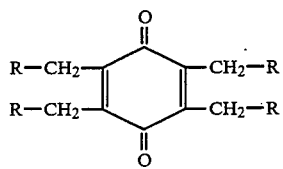

where R is bromine, $C_2$–$C_6$-acylthio or benzoylthio.

A preferred $C_2$–$C_6$-acylthio radical of the formula $CH_3$—$(CH_2)_{0-4}$—CO—S— is the acetylthio radical $CH_3$—CO—S—.

The present invention furthermore relates to a process for the preparation of the 2,3,5,6-tetrasubstituted p-benzoquinones of the formula I, wherein 2,3,5,6-tetramethylhydroquinone or 2,3,5,6-tetramethyl-p-benzoquinone is reacted with bromine at elevated temperatures with exposure to light, and, if desired, the resulting 2,3,5,6-tetra-(bromomethyl)-p-benzoquinone is reacted with a thiocarboxylic acid of the formula R'—H, where R' has the same meanings as R, with the exception of bromine.

The bromination of 2,3,5,6-tetramethylhydroquinone is advantageously carried out in the presence of a mercury lamp, in an inert solvent, preferably a halohydrocarbon, eg. carbon tetrachloride, chloroform, 1,1,1-trichloroethane, 1,1-dichloroethane, propylene chloride, perchloroethylene or tetrachloroethane, at from room temperature to 150° C., preferably from 50° to 80° C. The novel 2,3,5,6-tetra-(bromomethyl)-p-benzoquinone formed is isolated as a crystalline compound.

Instead of 2,3,5,6-tetramethylhydroquinone, 2,3,5,6-tetramethyl-p-benzoquinone can be brominated in a similar manner.

The 2,3,5,6-tetra-(bromomethyl)-p-benzoquinone is, if desired, reacted with a thiocarboxylic acid, eg. thiobenzoic acid or thioacetic acid, in an inert organic solvent, e.g. a hydrocarbon or an ether, in the presence of a base, e.g. an alkali metal carbonate, an alkaline earth metal carbonate or a metal hydroxide, at from 0° to 120° C., to give 2,3,5,6-tetra-(acylthiomethyl)-p-benzoquinone, which is isolated as a crystalline substance.

Finally, the present invention also relates to the use of the compounds of the formula I for the preparation of 4,8-dihydrobenzo[1,2-c:4,5-c']dithiophene-4,8-dione.

This reaction is carried out in the presence of a strong base, preferably an alkali metal hydroxide, in an inert organic solvent, preferably an alcohol, e.g. methanol or ethanol, or a diol, preferably ethylene glycol, compressed air being passed in at from 50° to 150° C., preferably from 70° to 100° C., to dehydrogenate the tetrahydro derivative initially formed.

2,3,5,6-tetra-(bromomethyl)-p-benzoquinone of the formula I can also be converted directly to 4,8-dihydrobenzo[1,2-c:4,5-c']dithiophene-4,8-dione by reaction with an anhydrous alkali metal sulfide in an inert organic solvent, preferably an alcohol or a diol, such as ethylene glycol, at from 50° to 150° C., followed by dehydrogenation of the tetrahydro derivative with sulfuryl chloride in an inert solvent, for example a halohydrocarbon, such as methylene chloride or chloroform.

In the latter, direct cyclization reaction to give 4,8-dihydrobenzo[1,2-c:4,5-c']dithiophene-4,8-dione, it is advantageous to exclude atmospheric oxygen and to carry out the reaction under an inert gas, e.g. nitrogen.

4,8-Dihydrobenzo[1,2-c:4,5-c']dithiophene-4,8-dione is a useful starting material for the preparation of the 5-substituted 9-cyanomethylenedithieno[3,4-b:4'3'-e]azepines described in European Laid-Open Application No. 0,050,212, and can be used to obtain these azepines in a simpler and more economical manner and in substantially better yield, especially in the case of fairly large batches.

The Examples which follow illustrate the invention.

EXAMPLE 1

2,3,5,6-Tetra-(bromomethyl)-p-benzoquinone

In a 2 liter stirred apparatus equipped with a Philips HPK 125 W mercury high pressure lamp, 40.0 g (240 millimoles) of 2,3,5,6-tetramethylhydroquinone in 1,200 ml of carbon tetrachloride were stirred and refluxed. After the lamp had been switched on, 204 g (1,272 millimoles) of bromine were added dropwise in the course of 45 minutes, the mixture being stirred thoroughly and refluxing being continued. Stirring was continued for a further hour with irradiation, and the reaction mixture was then transferred to a 2 liter conical flask. The product crystallized out on cooling. The mixture was cooled for 4 hours in an ice bath, after which the virtually colorless crystals were filtered off under suction. 91.4 g (79%) of product of melting point 169°–172° C. were iso- lated.

EXAMPLE 2

2,3,5,6-Tetra-(benzoylthiomethyl)-p-benzoquinone 44.0 g (320 millimoles) of finely powdered potassium carbonate were suspended in 350 ml of absolute toluene, and 19.2 g (40 millimoles) of finely powdered 2,3,5,6-tetra-(bromomethyl)-p-benzoquinone were added. 22.0 g (160 millimoles) of thiobenzoic acid were then added dropwise in the course of 5 minutes, while stirring thoroughly, after which the reaction mixture was slowly heated up. At an internal temperature of 60° C., the reaction began (dark coloration, increase in temperature and precipitation of solids). Heating was continued for a further 10 minutes at a bath temperature of 100° C., after which the mixture was allowed to cool, while stirring. In the final stage, cooling was carried out in an ice bath. The solid material was filtered off under suction and washed thoroughly with toluene and then with a large amount of water. 23.0 g (81%) of product of melting point 224°–226° C. were isolated.

EXAMPLE 3

2,3,5,6-Tetra-(acetylthiomethyl)-p-benzoquinone 41.3 g (300 millimoles) of finely powdered potassium carbonate were suspended in 350 ml of absolute toluene, while cooling with ice, and 18.0 g (37.5 millimoles) of finely powdered 2,3,5,6-tetra-(bromomethyl)- p-benzoquinone were added. 12.5 g (150 millimoles) of thioacetic acid were then added dropwise in the course of 5-7 minutes, while stirring thoroughly, after which the reaction mixture was stirred for a further hour in an ice bath, and the precipitated solids were filtered off under suction and washed with toluene and then with a large amount of water. 12.3 g (70%) of product of melting point 133°-135° C. were isolated.

USE EXAMPLES

Example A 48.5 g (68.5 millimoles) of 2,3,5,6-tetra-(benzoylthiomethyl)-p-benzoquinone were suspended in 450 ml of ethylene glycol, and 32.8 g (411 millimoles) of 50% strength sodium hydroxide solution were added, while stirring thoroughly. A strong jet of compressed air was then passed through the reaction mixture, and the latter was slowly heated up. At an internal temperature of 70° C., the dark mixture became homogeneous. The internal temperature was increased to 90°-100° C., and thorough stirring was continued at this temperature for 5 hours, while compressed air was continuously passed through. The mixture was cooled, 700 ml of water were added and stirring was continued for a further 0.5 hour, while cooling with ice. The solid material was filtered off under suction and washed with a large amount of water. 11.0 g (73%) of 4,8-dihydrobenzo[1,2-c:4,5-c']dithiophene-4,8-dione of melting point 340° C. were isolated.

Example B 250 ml of absolute ethylene glycol were introduced into a 0.5 liter stirred apparatus, the interior of which had been completely darkened with aluminum foil, and were heated to an internal temperature of 140°-150° C., under nitrogen. 9.6 g (20 millimoles) of 2,3,5,6-tetra-(bromomethyl)-p-benzoquinone and 3.9 g (50 millimoles) of anhydrous sodium sulfide (finely powdered in each case) were introduced in the course of 20 minutes via two metering apparatuses for solids, while stirring thoroughly. Stirring was continued for a further 45 minutes, after which the hot reaction mixture was filtered under suction, the residue was washed with hot ethylene glycol, the filtrate was poured into 3 liters of water and was acidified with dilute hydrochloric acid, while stirring, and the precipitated solid material was filtered off under suction and washed thoroughly with water. 4.0 g of the tetrahydro derivative were isolated. This was dried carefully and suspended in 200 ml of methylene chloride, and 2.9 ml (36 millimoles) of sulfuryl chloride were added to the stirred suspension. The mixture was stirred under reflux for a further hour, evaporated down to half its volume and cooled in an ice bath, and the precipitated solids were filtered off under suction. Further concentration of the mother liquor gave an additional precipitate. 1.1 g (25%) of 4,8-dihydrobenzo[1,2-c:4,5-c']- dithiophene-4,8-dione of melting point 340° C. were isolated.

We claim:

1. A 2,3,5,6-tetrasubstituted p-benzoquinone of the formula I

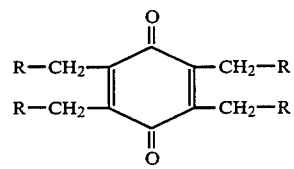

where R is bromine, $C_2$–$C_6$-acylthio or benzoylthio.

2. A compound of the formula I as defined in claim 1, wherein R is bromine.

3. A compound of the formula I as defined in claim 1, wherein R is benzoylthio.

4. A compound of the formula I as defined in claim 1, wherein R is acetylthio.

5. A process for the preparation of 2,3,5,6-tetra-(bromo-methyl)-p-benzoquinone which comprises: adding bromine to an inert solvent solution of 2,3,5,6-tetramethylhydroquinone or 2,3,5,6-tetra-methyl-p-benzoquinone, while exposing the solution to light.

6. The process of claim 5, wherein the solution is exposed to the light of a high pressure mercury lamp.

7. The process of claim 5, wherein the inert solvent is a halohydrocarbon.

8. The process of claim 5, wherein the temperature of the solution is between room temperature and 150° C.

9. The process of claim 5, wherein the temperature of the solution is between 50° and 80° C.

10. The process of claim 5, wherein bromine is added to a solution of 2,3,5,6-tetramethylhydroquinone.

11. The process of claim 10, wherein the solvent is carbon tetrachloride and wherein the temperature of the solution is maintained between 50° and 80° C.

* * * * *

UNITED STATES PATENT AND TRADEMARK OFFICE
CERTIFICATE OF CORRECTION

PATENT NO. : 4,562,004
DATED : December 31, 1985
INVENTOR(S) : Gerd STEINER

It is certified that error appears in the above—identified patent and that said Letters Patent is hereby corrected as shown below:

Title page:

PLEASE ADD:

[30] Foreign Application Priority Data

March 18, 1983 [DE] Fed. Rep. of Germany...... 3309719

Signed and Sealed this

Eighteenth Day of March 1986

[SEAL]

Attest:

DONALD J. QUIGG

Attesting Officer

Commissioner of Patents and Trademarks